United States Patent
Dasbach et al.

(10) Patent No.: US 10,300,202 B2
(45) Date of Patent: May 28, 2019

(54) MEDICAMENT CONTAINER CARRIER

(71) Applicant: Sanofi-Aventis Deutschland GMBH, Frankfurt am Main (DE)

(72) Inventors: Uwe Dasbach, Frankfurt am Main (DE); Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 3 days.

(21) Appl. No.: 14/435,596

(22) PCT Filed: Oct. 2, 2013

(86) PCT No.: PCT/EP2013/070583
§ 371 (c)(1),
(2) Date: Apr. 14, 2015

(87) PCT Pub. No.: WO2014/060215
PCT Pub. Date: Apr. 24, 2014

(65) Prior Publication Data
US 2015/0273153 A1     Oct. 1, 2015

(30) Foreign Application Priority Data
Oct. 16, 2012   (EP) ..................... 12188724

(51) Int. Cl.
*A61M 5/31*    (2006.01)
*A61M 5/20*    (2006.01)

(52) U.S. Cl.
CPC ............... *A61M 5/31* (2013.01); *A61M 5/20* (2013.01); *A61M 2005/2006* (2013.01); *F04C 2270/0421* (2013.01)

(58) Field of Classification Search
CPC .. A61M 2005/2006; A61M 5/20; A61M 5/31; A61M 2205/195; A61M 2205/368;
(Continued)

(56) References Cited

U.S. PATENT DOCUMENTS 5,462,740 A * 10/1995 Evenstad ............. A61K 9/0031
424/436
6,186,980 B1 * 2/2001 Brunel ................ A61M 5/3202
604/110
(Continued)

FOREIGN PATENT DOCUMENTS

| EP | 2468339 | 6/2012 |
|----|---------|--------|
| EP | 2468342 | 6/2012 |

(Continued)

OTHER PUBLICATIONS

Extended European Search Report in Application No. 12188724.4, dated Apr. 5, 2013, 7 pages.
(Continued)

*Primary Examiner* — Brandy S Lee
(74) *Attorney, Agent, or Firm* — Fish & Richardson P.C.

(57) ABSTRACT

A medicament container carrier comprising a proximal section having a first diameter, a distal section having a second diameter less than the first diameter, and at least one resilient beam arranged in the proximal section and having a beam head protruding radially to form a third diameter. The at least one beam has a non-deflected position in which the third diameter is less than the first diameter and a deflected position in which the third diameter is substantially equal to the first diameter.

19 Claims, 2 Drawing Sheets

(58) Field of Classification Search
CPC ........ A61M 2209/00; A61M 2209/045; A61M 5/1782; A61M 5/329; F04C 2270/0421
See application file for complete search history.

(56) References Cited

U.S. PATENT DOCUMENTS

2004/0127857 A1* 7/2004 Shemesh ............... A61M 5/326
604/198
2005/0277894 A1* 12/2005 Westbye ............. A61M 5/1782
604/198
2014/0243757 A1* 8/2014 Dasbach ................ A61M 5/20
604/221

FOREIGN PATENT DOCUMENTS

| JP | H02-5968 | 1/1990 |
|----|----------|--------|
| JP | 2003-511105 | 3/2003 |
| WO | WO 93/00949 | 1/1993 |
| WO | WO 2012/085033 | 6/2012 |

OTHER PUBLICATIONS

International Preliminary Report on Patentability in International Application No. PCT/EP2013/070583, dated Apr. 21, 2015, 7 pages.
International Search Report and Written Opinion in International Application No. PCT/EP2013/070583, dated Nov. 6, 2013, 10 pages.
Japanese Office Action in Application No. 2015-536070, dated Jul. 4, 2017, 4 pages.
European Communication in Application No. 13771161, dated Sep. 7, 2017, 4 pages.

* cited by examiner

MEDICAMENT CONTAINER CARRIER

TECHNICAL FIELD

The invention relates to a carrier for a medicament container.

BACKGROUND OF THE INVENTION

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Assembly of conventional injection devices can be time-consuming and costly, because components must be in certain orientation relative to other components. For example, a conventional medicament container carrier may require that a medicament container is in a predetermined angular orientation relative to the carrier for assembly. Re-orienting the container relative to the carrier may require time and expense, adding complexity and cost to the assembly process.

Thus, there remains a need for an improved medicament container carrier.

SUMMARY OF THE INVENTION

It is an object of the present invention to provide an improved medicament container carrier.

In an exemplary embodiment, a medicament container carrier according to the present invention comprises a proximal section having a first diameter, a distal section having a second diameter less than the first diameter, and at least one resilient beam arranged in the proximal section and having a beam head protruding radially to form a third diameter. The at least one beam has a non-deflected position in which the third diameter is less than the first diameter and a deflected position in which the third diameter is substantially equal to the first diameter.

In an exemplary embodiment, the beam head includes a proximal ramped surface.

In an exemplary embodiment, the beam head includes a distal surface parallel to a transverse axis of the carrier.

In an exemplary embodiment, the at least one beam includes a plurality of beams having a predetermined angular offset relative to each other.

In an exemplary embodiment, the medicament container carrier further comprises a medicament container. The medicament container is one of a cartridge and a syringe. The medicament container includes a barrel having a fourth diameter substantially equal to the second diameter and a flange having a fifth diameter substantially equal to the first diameter. The beam head is adapted to abut the flange when the beam is in the non-deflected position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
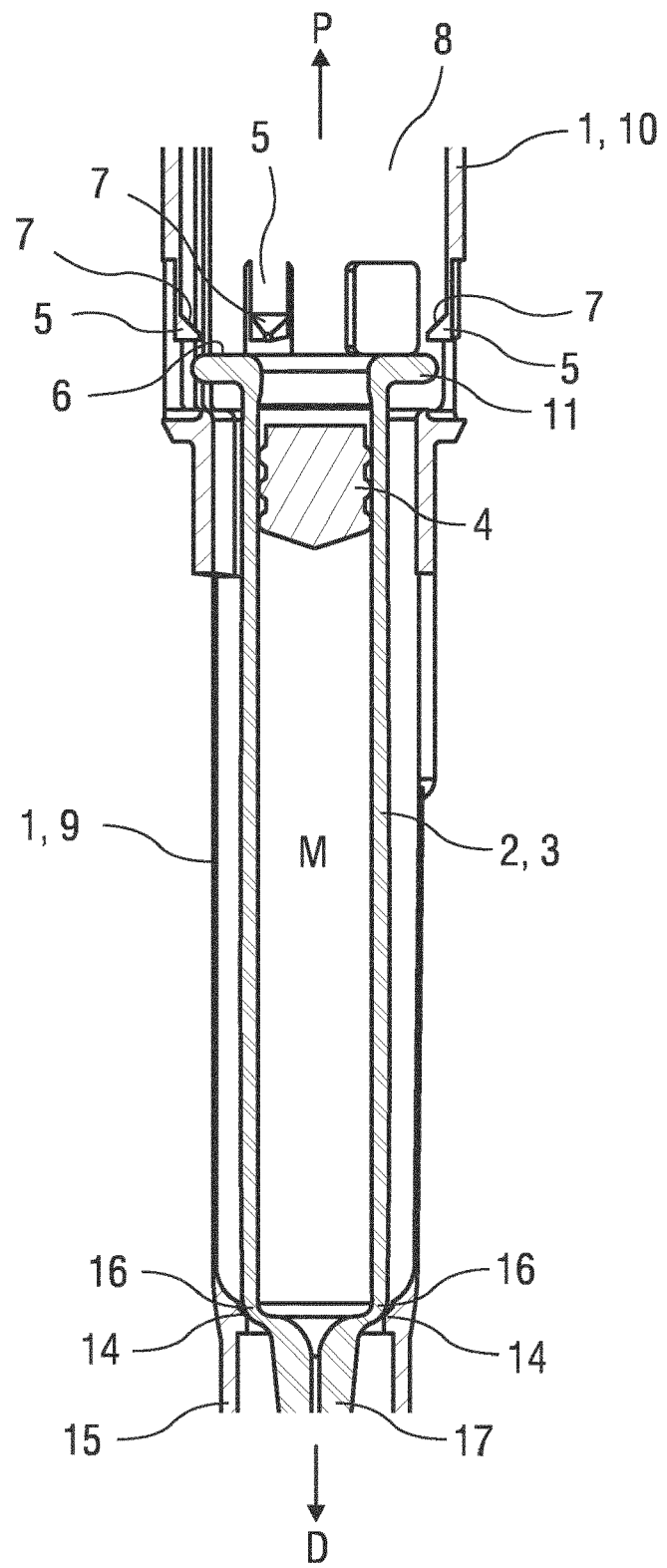
FIG. 1 is a schematic longitudinal section of an exemplary embodiment of a medicament container carrier according to the present invention.

FIG. 1 is a schematic longitudinal section of an exemplary embodiment of a medicament container carrier 1 according to the present invention. In the exemplary embodiment, the carrier 1 is adapted to hold a syringe 3. In other exemplary embodiments, the carrier 1 may be adapted to hold a cartridge, ampoule, reservoir or other medicament container. The syringe 3 comprises a barrel 2, a stopper 4 disposed in the barrel 2 and for sealing the syringe 3 distally and displacing a liquid medicament M through a needle. A proximal portion of the barrel 2 may include a flange 11 which projects radially. A diameter of the flange 11 may be greater than the diameter of the barrel 2. The flange 11 may extend radially from an entire circumference or only portions of the circumference of the proximal portion of the barrel 2.

In the exemplary embodiment shown in FIG. 1, the carrier 1 includes a proximal section 10 and a distal section 9. The proximal section 10 may have a diameter which is substantially equal to the diameter of the flange 11. The distal section 9 may have a diameter which is substantially equal to the diameter of the barrel 2.

In an exemplary embodiment, a distal portion of the proximal section 10 of the carrier 1 includes at least one resilient beam 5 having a beam head 7 with a proximal ramped surface which is angled radially toward a longitudinal axis of the carrier 1 and a distal surface parallel to a proximal surface 6 of the flange 11 and a transverse axis of the carrier 1. The beam 5 has a non-deflected position, in which the beam head 7 protrudes radially toward the longitudinal axis of the carrier 1, thus decreasing an effective diameter of the proximal section 10 of the carrier 1. The beam 5 has a deflected position in which the beam head 7 is displaced radially, thus enlarging the effective diameter of the proximal section 10 of the carrier 1. When the beam 5 is in the non-deflected position, the beam head 7 reduces the effective diameter of the proximal section 10 of the carrier 1 to a diameter substantially equal to or less than the diameter of the flange 11 but substantially equal to or greater than the diameter of the barrel 2.

Figure 2:
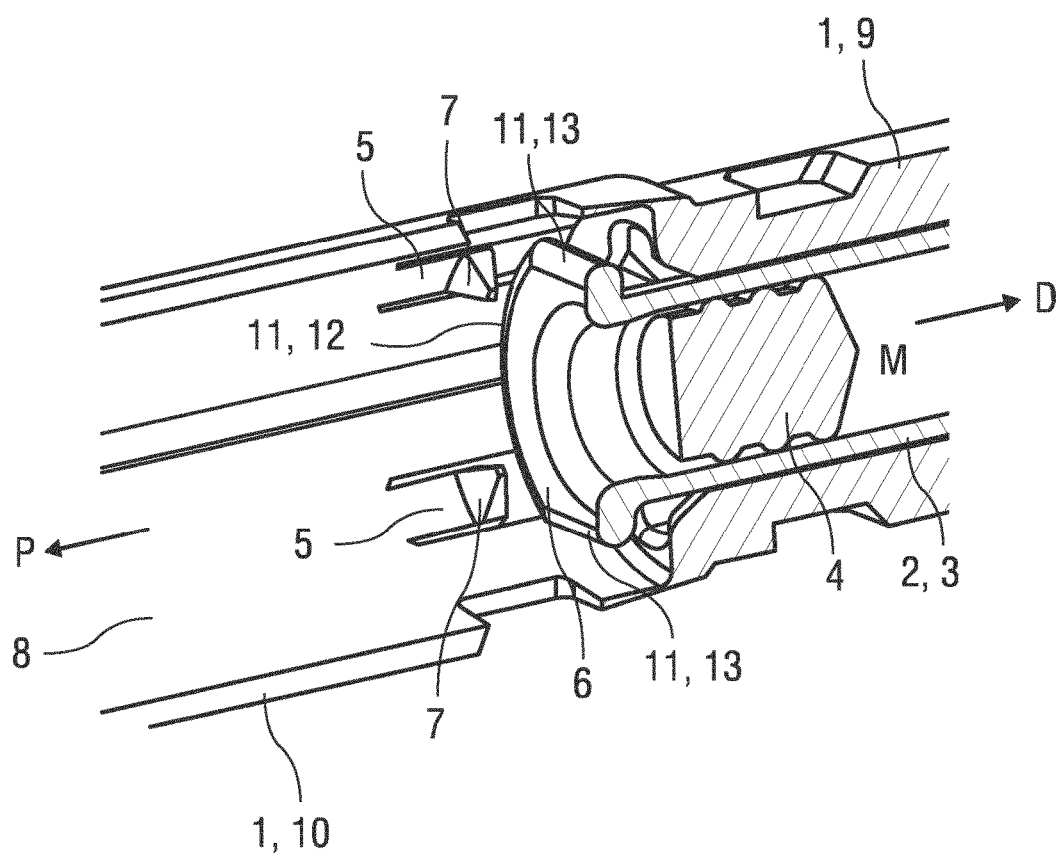
FIG. 2 is a perspective detail view of an exemplary embodiment of a medicament container carrier according to the present invention.

In an exemplary embodiment in which the carrier 1 includes a plurality of beams 5, an angular offset between neighboring beams 5 may be a predetermined angle (e.g., about 90°) or different angles. The beams 5 are aligned on the carrier 1 so that the syringe 3 is restrained within the syringe carrier 1 regardless of the angular position of the syringe 3 and the carrier 1, because at least one of the beams 5 abut the flange 11, as shown in FIG. 2.

Referring back to FIG. 1, the exemplary embodiment of the carrier 1 may include a front stop 14 arranged near a distal end 15 of the carrier 1 for abutting a distal shoulder 16 of the syringe 3 between the barrel 2 and a neck 17 to limit axial movement of the syringe 3 within the carrier 1 in a distal direction D. Supporting the syringe 3 at the distal end instead of at the flange 11 may prevent damage to the flange 11 when the stopper 4 is subjected to load for displacing the medicament M from the barrel 2.

During assembly, the syringe 3 is inserted into the proximal section 10 of the carrier 1. As the syringe 3 translates relative to the carrier 1 in the distal direction, the beams 5 are in the non-deflected position and the barrel 2 slides through the proximal section 10. When the flange 11 abuts the beam head 7, a distally-directed force is applied to the syringe 3, causing the beam 5 to move to the deflected position and allow passage of the flange 11. The proximal ramped surface of the beam head 7 reduces the force necessary to deflect the beam 5. After the flange 11 has passed the beam head 7, the beam 5 returns to the non-deflected position. The distal surface of the beam head 7 may act as an abutment surface to prevent translation of the syringe 3 in the proximal direction relative to the carrier 1. For example, during delivery of the medicament M and after-use the syringe 3 is positioned by a pressure applied to the stopper 4 forcing the syringe 3 forwards against the front stop 14 in the carrier 1. The beam 5 in the carrier 1 prevents a so called wet injection, i.e. medicament leaking out of the needle during needle insertion, as the syringe 3 is advanced and the needle inserted into the injection site by advancing the carrier 1 without applying pressure to the stopper 4.

Furthermore the beam 5 in the carrier 1 ensures that any movement of the syringe 3 during re-capping, i.e. re-attaching a needle boot and/or a device cap, prior to injection is not perceived by the user.

As the beam 5 is compliant, the probability of damage to the flange 11 during needle insertion is reduced.

While the exemplary embodiments have been described using terms such as "circumference" and "diameter" implying that the described components are circular or cylindrical, those of skill in the art will understand that the components may be any appropriate size or shape and have varying cross-sectional areas and geometries.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament container carrier comprising:
a proximal section having a first diameter;
a distal section having a second diameter less than the first diameter; and
at least one resilient beam arranged in the proximal section of the medicament carrier, the at least one resilient beam extending distally from the proximal section of the medicament carrier and the at least one resilient beam having a beam head located at a distal end of the at least one resilient beam and protruding radially to form a third diameter, the beam head being arranged to abut a flange at a proximal end of a medicament container to inhibit translation of the medicament container in the proximal direction,
wherein the at least one resilient beam has a non-deflected position in which the third diameter is less than the first diameter and greater than the second diameter and a deflected position in which the third diameter is substantially equal to the first diameter.

2. The medicament container carrier of claim 1, wherein the beam head comprises a proximal ramped surface.

3. The medicament container carrier of claim 1, wherein the beam head comprises a distal surface parallel to a transverse axis of the carrier.

4. The medicament container carrier of claim 1, wherein the at least one resilient beam comprises a plurality of resilient beams having a predetermined angular offset relative to each other.

5. The medicament container carrier of claim 4, wherein the predetermined angular offset is 90 degrees.

6. The medicament container carrier of claim 1, further comprising:
a medicament container.

7. The medicament container carrier of claim 6, wherein the medicament container is selected from a group consisting of: a cartridge, an ampoule, a reservoir, and a syringe.

8. The medicament container carrier of claim 6, wherein the medicament container comprises a barrel having a fourth diameter substantially equal to the second diameter and the flange having a fifth diameter substantially equal to the first diameter.

9. The medicament container carrier of claim 8, wherein the beam head is configured to abut the flange when the resilient beam is in the non-deflected position.

10. The medicament container carrier of claim 8, further comprising a front stop arranged on the distal section of the medicament container carrier, the front stop configured to support a distal shoulder of the medicament container.

11. The medicament container carrier of claim 1, wherein the at least one resilient beam is integrally formed with the proximal section.

12. The medicament container carrier of claim 1, wherein the proximal section comprises a cylindrical wall.

13. An autoinjector comprising:
a medicament container carrier, the medicament container carrier comprising:
a proximal section having a first diameter,
a distal section having a second diameter less than the first diameter, and
at least one resilient beam arranged in the proximal section of a medicament container carrier, the at least one resilient beam extending distally from the proximal section of the medicament carrier and the at least one resilient beam having a beam head located at a distal end of the at least one resilient beam and protruding radially to form a third diameter, the beam head being arranged to abut a flange on a proximal end of a medicament container to inhibit translation of the medicament container in the proximal direction, wherein the at least one resilient beam has a non-deflected position in which the third diameter is less than the first diameter and greater than the second diameter and a deflected position in which the third diameter is substantially equal to the first diameter; and wherein the autoinjector is configured to provide a force for administering an injection of a medicament from a medicament container held by the medicament container carrier.

14. The autoinjector of claim 13, further comprising:
a medicament container removably supported within the medicament container, the medicament container comprising:
a barrel,
a stopper disposed in the barrel, and
a needle at a distal end of the barrel.

15. The autoinjector of claim 14, wherein the medicament container is selected from a group consisting of a cartridge, an ampoule, a reservoir, and a syringe.

16. The autoinjector of claim 14, further comprising:
a spring to provide the force against the stopper for administering an injection, and
an activation mechanism that, upon activation, releases the spring such that the stopper advances through the barrel to deliver a liquid medicament contained within the medicament container through the needle.

17. The autoinjector of claim 14, wherein the medicament container comprises a barrel having a fourth diameter substantially equal to the second diameter and the flange having a fifth diameter substantially equal to the first diameter.

18. The autoinjector of claim 17, wherein the beam head is configured to abut the flange when the resilient beam is in the non-deflected position.

19. The autoinjector of claim 17, wherein the medicament container carrier further comprises a front stop arranged on the distal section of the medicament container carrier, the front stop configured to support a distal shoulder of the medicament container.

* * * * *